(12) United States Patent
Doerr et al.

(10) Patent No.: US 8,781,588 B2
(45) Date of Patent: Jul. 15, 2014

(54) MRT OPTOCOUPLER

(75) Inventors: Thomas Doerr, Berlin (DE); Ingo Weiss, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 811 days.

(21) Appl. No.: 12/970,290

(22) Filed: Dec. 16, 2010

(65) Prior Publication Data

US 2011/0152672 A1 Jun. 23, 2011

Related U.S. Application Data

(60) Provisional application No. 61/288,856, filed on Dec. 22, 2009.

(51) Int. Cl.
*A61B 5/05* (2006.01)
*A61N 1/37* (2006.01)

(52) U.S. Cl.
CPC .............. *A61N 1/37* (2013.01); *A61N 1/3718* (2013.01)
USPC ............................................ 607/36; 600/421

(58) Field of Classification Search
USPC ............................................................ 607/36
See application file for complete search history.

(56) References Cited

U.S. PATENT DOCUMENTS

| | | |
|---|---|---|
| 7,164,950 B2 | 1/2007 | Kroll et al. |
| 7,450,996 B2 | 11/2008 | MacDonald et al. |
| 2002/0128691 A1* | 9/2002 | Connelly .................... 607/36 |
| 2003/0195570 A1 | 10/2003 | Deal et al. |
| 2003/0204217 A1* | 10/2003 | Greatbatch ................. 607/36 |
| 2004/0088012 A1 | 5/2004 | Kroll et al. |
| 2005/0043761 A1 | 2/2005 | Connelly et al. |
| 2005/0090886 A1 | 4/2005 | MacDonald et al. |
| 2006/0293591 A1* | 12/2006 | Wahlstrand et al. .......... 600/423 |
| 2007/0239231 A1* | 10/2007 | Ginggen ..................... 607/63 |
| 2008/0154342 A1* | 6/2008 | Digby et al. ................ 607/63 |
| 2008/0208276 A1 | 8/2008 | Wedan |
| 2009/0138058 A1* | 5/2009 | Cooke et al. ................. 607/5 |

OTHER PUBLICATIONS

Yang, K. et al., High-Resolution Electro-Optic Mapping of Near-Field Distributions in Integrated Microwave Circuits, Microwave Symposium Digest, 1998 IEEE MTT-S International vol. 2, Issue 7-12, Jun. 1998, pp. 949-952, vol. 2, Digital Object Identifier 10.1109/MWSYM.1998.705148.
European Search Report dated Jan. 5, 2012 (6 pages).

* cited by examiner

*Primary Examiner* — Carl H Layno
*Assistant Examiner* — Jennifer Ghand
(74) *Attorney, Agent, or Firm* — ARC IP Law, PC; Joseph J. Mayo

(57) ABSTRACT

Device and method for detecting electromagnetic fields occurring in imaging magnetic resonance tomography MRT/MRI tests. Relates to an implantable medical device (IMD) comprising a hermetically sealed housing, control unit(s), detection unit(s) for MRT interference fields connected/connectable to control unit(s) and to electrode(s) and/or to antenna(s) and/or coil(s), wherein the MRT interference detection unit contains at least one electro-optical converter which converts induced voltages from the electrode(s) and/or the antenna(s) and/or the coil(s) to optical signals, which are optically transmitted in a potential-free manner within the detection unit for MRT interference fields to an evaluation unit for the detection unit for MRT interference fields, and when a threshold for the optical signal and/or a predetermined periodic occurrence of the optical signals is exceeded, the evaluation unit triggers switching to an MRI-safe state or transmits a corresponding signal to the control unit(s).

21 Claims, 6 Drawing Sheets

MRT OPTOCOUPLER

This application claims the benefit of U.S. Provisional Patent Application 61/288,856 filed 22 Dec. 2009, the specification of which is hereby incorporated herein by reference.

BACKGROUND OF THE INVENTION

1. Field of the Invention

Embodiments of the invention relate to a device and a method for detecting electromagnetic fields, in particular fields occurring in imaging magnetic resonance tomography tests (referred to herein as "MRT" or "MRI" which stand for magnetic resonance tomography and magnetic resonance imaging respectively, wherein these two acronyms are used interchangeably herein).

2. Description of the Related Art

Although MRI testing is becoming increasingly important in diagnostic medicine, it is contraindicated for some patients. Such contraindication may result from an active implanted medical device (also referred to below as "implant" or "IMD"). Besides MRI testing, however, other technical applications pose a risk to the user of medical devices or implantable medical devices, particularly when such applications generate strong electromagnetic interference (EMI) fields in their surroundings.

In order to still allow MRI testing, various approaches are known which relate either to performing the MRI testing or to the implantable medical device.

Among others, technologies based on conventional processes for identifying magnetic fields are known for detecting magnetic fields. U.S. 2008/0154342 describes a method which uses a giant magnetoresistance (GMR) sensor to detect problematic magnetic fields from MRT devices. However, these technological approaches are not very specific, and create increased energy requirements which result in a shorter operating period for equivalent energy reserves.

A further technological approach is the use of optical signal transmission instead of typical electrode lines based on electrical signal transmission. Use of these optical lines prevents the coupling of electromagnetic interference fields from an MRI device into the electrode lines, but the overall system is more complex since on the one hand the electrical signals must first be converted to optical signals, and on the basis of the signals the stimulation pulses must be generated from the optical signals at the stimulation site, and on the other hand signals that are measured at the stimulation site must likewise be converted. As a rule, such higher-complexity systems also increase the energy requirements for an implant. Such a system based on optical signal transmission is described in U.S. 2005/0090886 and U.S. Pat. No. 7,450,996.

BRIEF SUMMARY OF THE INVENTION

The object of one or more embodiments of the invention is to provide an implantable medical device which allows reliable and safe detection of MRT interference fields. The object is achieved by use of an implantable medical device (IMD) having the features as claimed herein.

The implantable medical device (IMD) contains at least one hermetically sealed housing, at least one control unit, at least one MRT interference field detection unit which is connected or connectable to at least one control unit and to at least one electrode and/or to at least one antenna and/or at least one coil, wherein the MRT interference detection unit has at least one electro-optical converter which converts the induced voltages from the at least one electrode and/or the at least one antenna and/or the at least one coil to optical signals, which are optically transmitted in a potential-free manner within the MRT interference field detection unit to an evaluation unit for the MRT interference field detection unit, and when a threshold for the optical signal and/or a predetermined periodic occurrence of the optical signals is exceeded, the evaluation unit triggers switching to an MRI-safe state or transmits a corresponding signal to the at least one control unit.

The MRT interference field detection unit may also have a modular design; i.e., as an example but not limited thereto, the electro-optical converter may also be localized, also spatially separated from the remainder of the MRT interference field detection unit, and the light signals may be transmitted via optical conductors, such as but not limited to glass fibers, to the MRT interference detection unit. Other components of the MRT interference detection unit may also be spatially separated from same; for longer distances an optical signal line is preferred over the electrical signal line.

It is also preferred that electro-optical converters emit at different frequencies, and in particular for various receivers multiple emission frequencies may be used, also to allow differentiation of the induced voltages according to site of generation, and to include this information in the evaluation. Differentiated reactions to the occurrence of MRT interferences are thus possible, depending on which elements of the IMD and/or of the associated electrode lines and/or electrodes are affected.

It is further preferred that the detection unit for MRT interference fields has at least one sensor which converts the optical signals from at least one electro-optical converter to electrical signals which are used for the MRT detection, whereby the signals from multiple electro-optical converters may also be sent to a sensor.

It is likewise preferred that at least one electrode is present which is used for therapeutic and/or or diagnostic purposes, whereby the electrode may extend outside the hermetically sealed housing, or may be situated on the exterior of this housing or may be a part of this housing.

In a further preferred embodiment the at least one electrode is a connection to at least one sensor and/or at least one actuator distally situated with respect to the implant.

It is also preferred that the electro-optical converter is an optocoupler.

It is particularly preferred that the electro-optical converter is a sensor for electromagnetic fields which is based on the Kerr effect.

It is further preferred that the electro-optical converter is a sensor for electromagnetic fields which is based on the optical properties of a crystal which depend on external electromagnetic fields. One example of such a system that is suited for this type of sensor is found in $LiTaO_3$→High-Resolution Electro-Optic Mapping of Near-Field Distributions in Integrated Microwave Circuits, K. Yang, G. David, S. Robertson, J. F. Whitaker, and L. P. B. Katehi, Microwave Symposium Digest, 1998 IEEE MTT-S International Volume 2, Issue 7-12, June 1998, pages 949-952, Vol. 2, Digital Object Identifier 10.1109/MWSYM.1998.705148.

It is also preferred that the electro-optical converter is situated inside or outside, or in a housing leadthrough, of the hermetically sealed housing.

It is likewise preferred that the electro-optical converter transfers only information concerning the amplitudes and/or amplitude envelopes and/or the frequencies, and/or phases, in the case of multiple electro-optical converters.

It is particularly preferred that the detection unit for MRT interference fields determines from the optical signal a scalar value which represents the identified field intensity, and when a presettable and/or variable threshold value is exceeded or when a presettable and/or variable threshold value range is reached the detection unit identifies an MRT field, whereby the scalar value may also be a functional or logical linkage composed of one or more information items, such as amplitude information and/or frequency information and/or phase information, or weighted information.

In a further preferred embodiment the information is weighted by predetermined damping of the optical signals during transmission of the optical signals, whereby additional different dampings for different signal sources or types of information over various transmission frequencies may be achieved.

It is further preferred that multiple electrical feed lines are connected to the electro-optical converter in series and/or in parallel.

It is also preferred that the electro-optical converter is connected to at least one protective element in series and/or in parallel. Examples of protective elements include but are not limited to EMI capacitors and/or protective diodes.

It is likewise preferred that the optical converter is connected between two feed lines, wherein the term "feed lines" includes, in addition to electrical lines, flat electrodes such as the implant housing.

It is also preferred that the threshold value for MRT detection is a weighted function of the determined frequency of the induced voltages, and/or the threshold value and/or the weighting factors is/are a function of static field intensity determined using other sensors or indicators, wherein the functional dependency may be linear or nonlinear.

It is further preferred that the MRT-safe state that is switched on or initiated by the MRT interference detection unit is switched on for a predetermined or predeterminable time, and after the time elapses is deactivated, or another MRT detection is performed.

It is also preferred that MRT detection takes place only when, concurrently with the MRT detection, at least one additional measurement method (using a corresponding sensor for example) also signals MRT detection, wherein additional methods are understood to mean, but are not limited to, the following methods: GMR sensors, MagFET sensors, Hall sensors, monitoring of battery voltages during capacitor charging processes, detection of RF fields, detection of magnetic gradient fields, detection of currents induced by electromagnetic fields, and detection of specific vibrations, or components designed as sensors for detection of vibrations induced by Lorentz forces.

It is likewise preferred that at least one of the following measures is introduced for MRT detection or by the MRT detection signal: Changing to an MRI-safe state, remaining for a prolonged period of time in an MRI-safe state or a state that is insensitive to electromagnetic interference fields, synchronization of electrical measurements (impedance measurements, for example) using field intensity minimum values occurring with periodic or pulsed electromagnetic fields, or synchronization of a stimulation using these same minimum values, and emission of electromagnetic pulses for signaling that a medical device, in particular an implant, is present in the electromagnetic field, in particular for signaling to an MRI device, with the possibility of thus transmitting information as well as the interference and displaying same on the MRI screen.

It is further preferred that a position sensor is used for plausibility checking, and a positive MRI identification is made only when the position sensor reports a prone posture and/or another presettable posture.

The position sensor is particularly preferably self-calibrating, the calibration taking place under presettable boundary conditions such as, but not limited to, times of day and/or heart rates and/or respiratory rate and/or hemodynamic parameters and/or activity (motion sensor).

BRIEF DESCRIPTION OF THE DRAWINGS

Several aspects of the invention are illustrated in FIGS. 1 through 6.

DETAILED DESCRIPTION OF THE INVENTION

Figure 1:
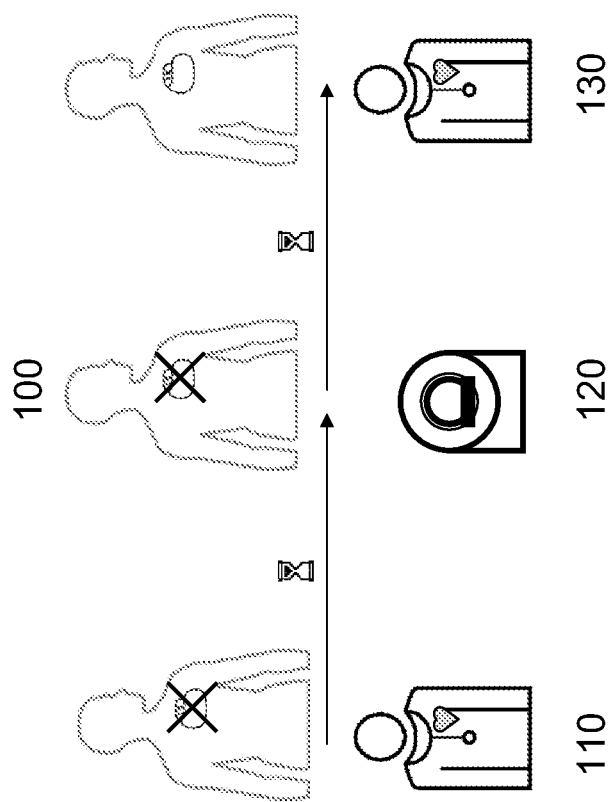
FIG. 1 shows a schematic illustration of the sequence of an MRT test.

FIG. 1 describes the prior art, in which the ICD patient 100 receives follow-up care from a cardiologist before the planned MRT test, and the ICD is switched off 110. After a time delay of hours to days the MRT test is performed by a radiologist 120. After a further delay the patient is once again under the care of the cardiologist 130, and the ICD is switched back on. During the entire time from 110 to 130 the patient is without the protection of the implanted defibrillator, and is essentially without rhythm monitoring. This residual risk is currently accepted in return for the benefits of the MRT test.

Figure 2:
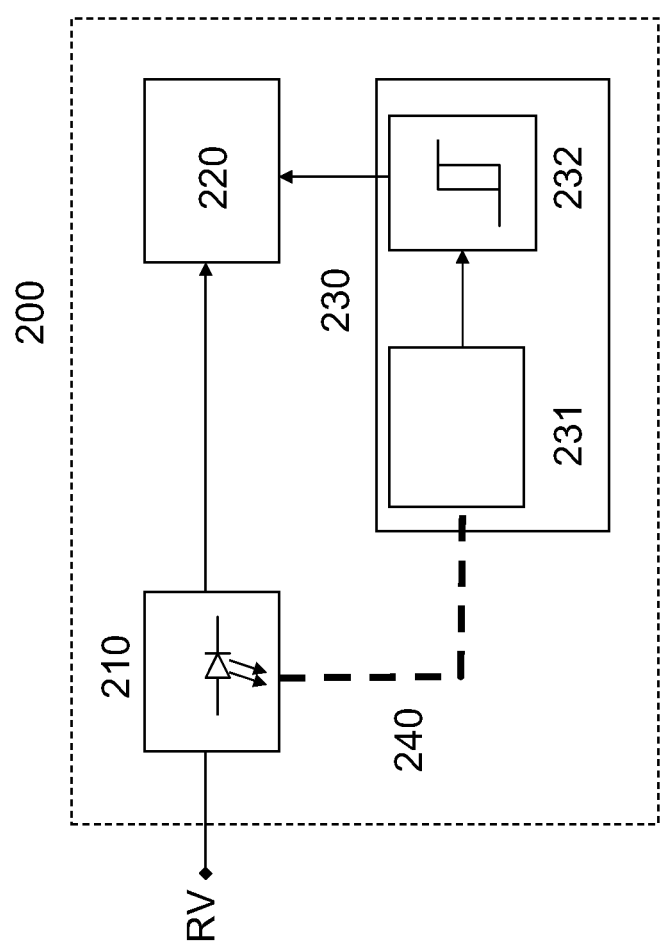
FIG. 2 shows a block diagram of an implant according to the invention, having an electro-optical converter for detecting electromagnetic interference fields.

FIG. 2 shows a block diagram of the approach according to the invention for detecting strong magnetic fields, in particular variable electromagnetic fields. For simplicity this exemplary embodiment refers to a single-chamber pacemaker. Embodiments as a multichamber pacemaker, ICD, CRT device, medication pump, monitoring device for physiological bodily functions, and/or neurostimulator represent simple variations for one skilled in the art, and are easily achievable. The term "implant" below refers to an implantable medical device according to the invention. The electrode line RV passes through a leadthrough into the interior of the implant 200. In the implant 200 the electrical signals are relayed to the implant electronics system via an electro-optical converter. If electromagnetic interference fields of a predeterminable intensity are present, the electro-optical converter emits light, which is relayed via the light guide or optical link 240 to a control unit 230. The control unit 230 contains at least one optical sensor 231 which is connected to the optical conductor, and contains a threshold value comparator 232 which is connected to the optical sensor 231. The threshold value comparator 232 compares the signal from the optical sensor 231 to one or more presettable threshold values, and as a result of the comparison sends either a signal to the implant electronics system 220 as to whether one or more presettable threshold values have been exceeded, and/or a signal that indicates the extent by which a presettable threshold value has been exceeded. As a response by the implant electronics system 220 to the signal from the control unit 230, or more precisely, from the threshold value comparator 232, the implant electronics system 220 changes a presettable operating mode which allows the implant to operate without problems under the given electromagnetic influences.

In another possible design, the MRT RF field or some other electromagnetic interference excites an LED, attached to the leadthrough of the implant or at another location inside or outside the implant, to emit optically detectable electromagnetic radiation. Simply stated, this means that the emission of light indicates that MRT or another strong electromagnetic field having a risk potential similar to MRT is present in the surroundings of the implant 200. This LED may be a component of either an optocoupler 210 or of the protective transistors (arrays) which are necessary anyway, and the electrodes and the housing decouple from the implant electronics system 220 whenever the LED is lit. This approach is particularly useful for implants having no, or inadequate, filtered leadthroughs. If the filtered leadthroughs are in fact adequate for protecting the electronics system from high RF voltages, this LED may be installed in the implant header, i.e., in the connecting segment of the implant which is usually made of plastic, by use of the leads which connect the leadthroughs in the implant 200 to the electrodes RV (or may be installed further in the distal direction), and the information may be sent without interference via an optical leadthrough into the interior, where mechanisms to protect against other electromagnetic fields are switched on.

The RF detection, which is free of a reference potential and which eliminates the risk of demodulation in the implant, is advantageous. Thus, the EMI capacitors may also be dispensed with, and the requirements of a hemodynamic sensor (HDS) and MRT may be combined in a single ICD/IPG.

Furthermore, one design allows the electrode interface to be disconnected in the presence of RF interference in the MRT or from other electromagnetic interference sources, whereby the remaining coupling of the RF interference into the interior of the implant is very minimal. According to the invention, the electrical component of the interference field is used for identifying same, in contrast to U.S. Pat. No. 7,164,950 B2, in which inductive sensing of the high-frequency interference fields inside a highly conductive (metallic, for example) housing would not be possible.

Figure 3:
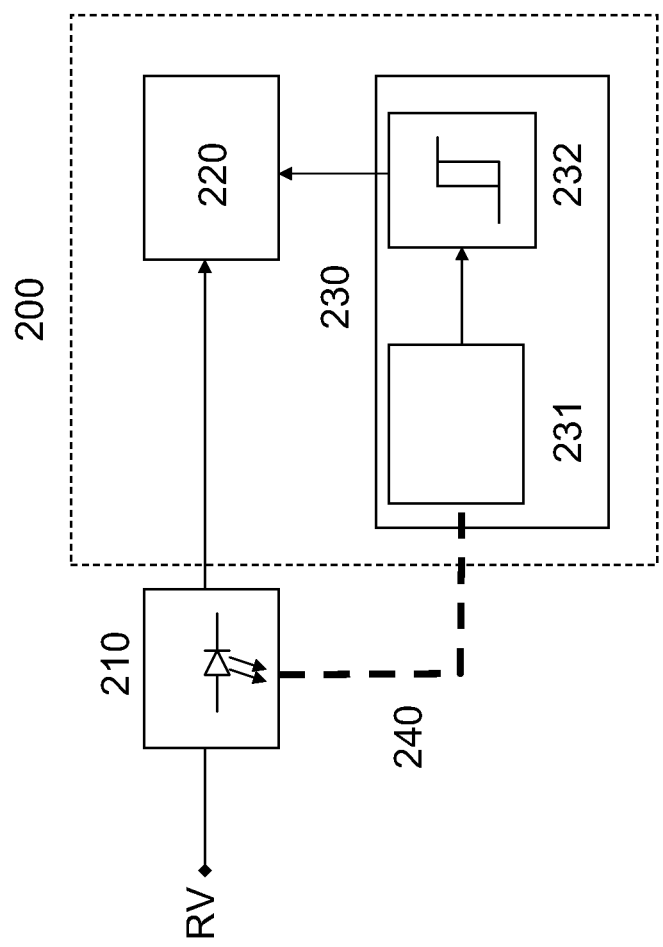
FIG. 3 shows a block diagram of an implant according to the invention, having an electro-optical converter for detecting electromagnetic interference fields.

FIG. 3 shows an embodiment in which the electro-optical converter 210 is situated outside the implant 200. In other respects the design is analogous to that in FIG. 2, except that, due to the position of the electro-optical converter 210, it is necessary to have an optical leadthrough on the implant which conducts the optical signals into the interior of the implant.

Figure 4:
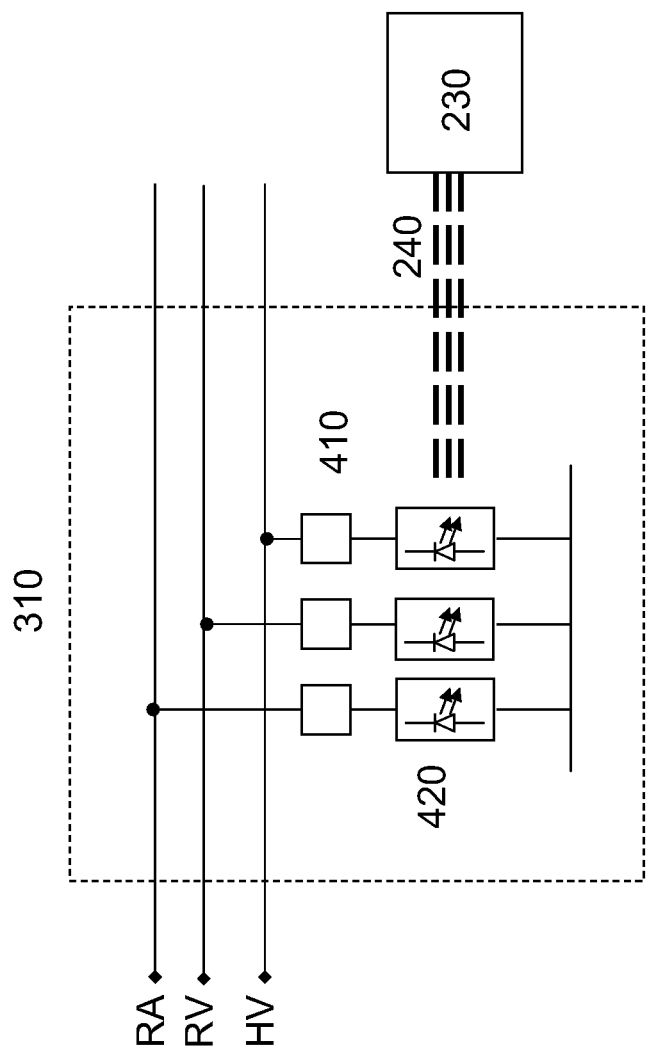
FIG. 4 shows a block diagram of an input protection circuit according to the invention.

The embodiment shown in FIG. 4 refers to a dual-chamber pacemaker with a defibrillator. The necessary lines are denoted by RV (right ventricle), RA (right atrium), and HV (shock electrodes), which are connected to the input protection circuit 310. The input protection circuit contains multiple protective elements, in the present case preferably three protective elements 410, i.e., one protective element 410 for each electrode line (RV, RA, and HV), which is respectively connected to an electrode line, and multiple electro-optical converters 420, in the present case preferably three electro-optical converters 420, respectively connected to a protective element 410. In addition, a light guide 240 respectively leads from each of the three electro-optical converters 420 to a control unit 230. The advantage of this design, among others, is that the control unit 230 is able to react differently to the various signals on the individual electrode lines (RA, RV, and HV), and also different modes may be selected from the implant control system 220 (not shown in FIG. 4). The different modes may preferably bring about different measures for some or all of the electrode lines and/or the entire implant and/or individual components of the implant.

Figure 5:
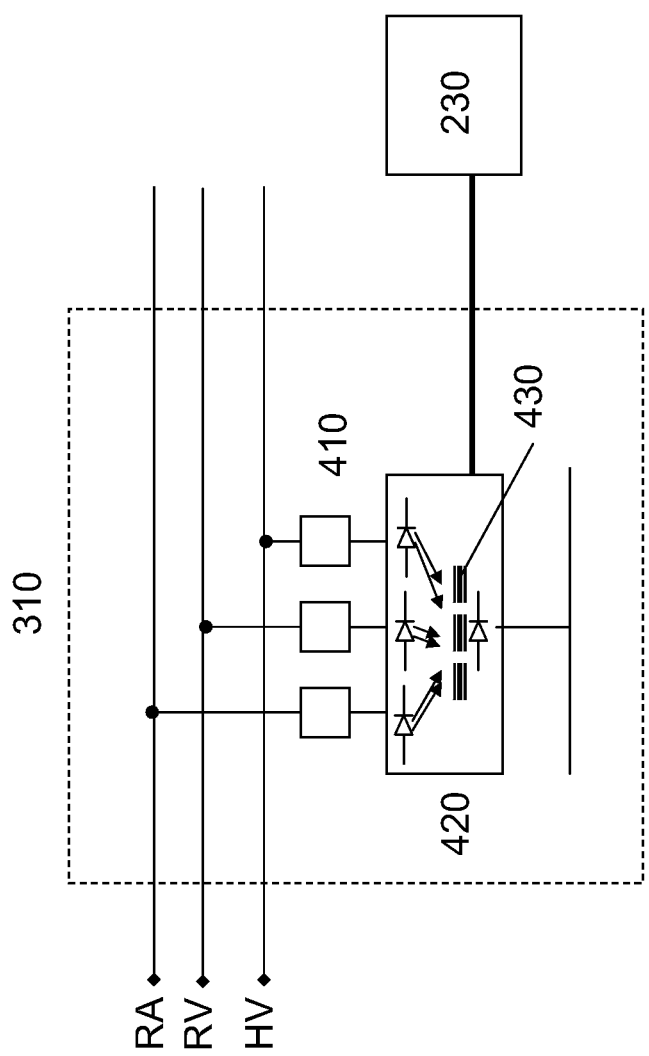
FIG. 5 shows a block diagram of an input protection circuit according to the invention, having a weighting filter.

The design shown in FIG. 5 is analogous to that in FIG. 4, except that the optical signals are transmitted differently. The essential difference is that each electro-optical converter 420 also has a weighting filter 430. The light-emitting elements (LEDs) illuminate the same sensor. This corresponds to an OR operation. In order to take into account the importance of the individual contributions of various implant inputs with regard to the coupled interference, the optical signals are weighted. This is carried out using an optical filter whose damping, which may be set separately for each light-emitting element, produces the weighting factors based on the importance of individual inputs.

Figure 6:
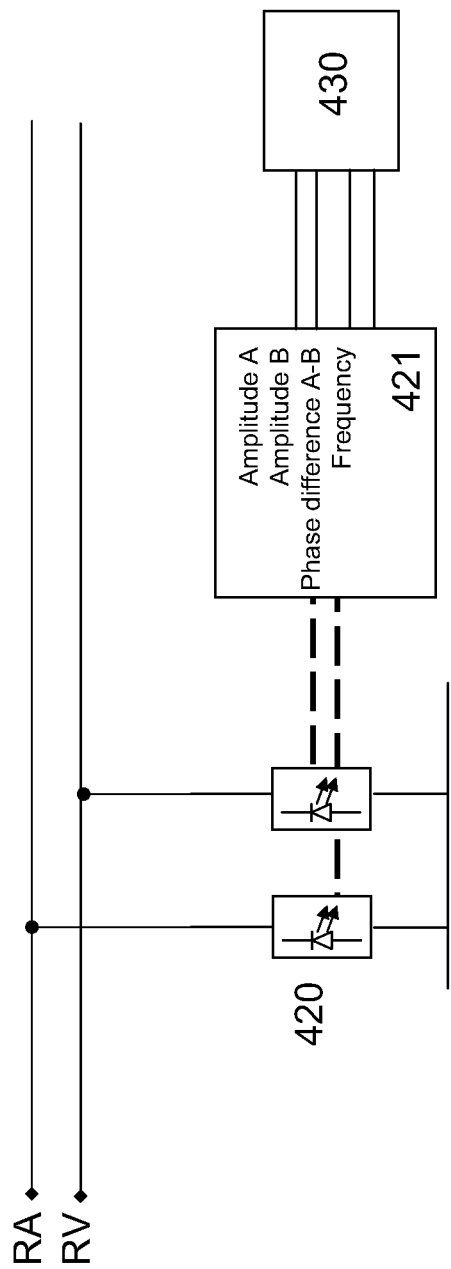
FIG. 6 shows a block diagram of a complex input protection circuit according to the invention.

In a further design shown in FIG. 6, the detected and induced signals, the same as for the previous examples, are relayed from the electrode lines (only two of which (RA and RV) are shown here for simplicity, although there may be more) to a respective electro-optical converter 420. The optical signals emitted by the electro-optical converter are then sent via an optical conductor to a further electro-optical converter 421, which on the basis of the signal determines amplitudes and/or frequencies and/or phase relationships and relays these to the control unit 430. The data determined by the second electro-optical converter are evaluated by the control unit by means of a threshold value comparator, and the result is further processed analogously to the procedure in FIG. 2.

The described designs allow the presence of MRT or other high-frequency strong electromagnetic fields, for example for patients in the vicinity of transmitters such as a wireless relay station, to be reliably detected by an electronic implant so that the implant is able to switch to an (MRT) safe state. The aim of the invention is to ensure that the RF interference produced by MRT results in little or no coupling into the electronic circuit of the implant.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
    a hermetically sealed housing;
    at least one control unit situated within said hermetically sealed housing;
    at least one conducting element coupled with said implantable medical device wherein said at least one conducting element comprises any combination of one or more of
        at least one electrode,
        at least one antenna,
        at least one coil;
    at least one detection unit configured to detect magnetic resonance tomography interference fields which is connected to the at least one control unit and to said at least one conducting element;
    an evaluation unit coupled with the at least one detection unit;
    wherein the at least one detection unit contains
        at least one electro-optical converter configured to convert induced voltages for said magnetic resonance tomography interference fields from said at least one conducting element to optical signals, which are optically transmitted in a potential-free manner within the detection unit to the evaluation unit; and, wherein when one or more of a threshold for the optical signals and a predetermined periodic occurrence of the optical signals is exceeded, the evaluation unit is configured to trigger the implantable medical device to switch to a magnetic resonance imaging-safe state.

2. The implantable medical device according to claim 1, wherein said at least one electro-optical converter comprises multiple electro-optical converters, wherein the at least one detection unit for magnetic resonance tomography interference fields has at least one sensor configured to convert the optical signals from said at least one electro-optical converter to electrical signals which are used for the magnetic resonance tomography detection, and wherein the optical signals from said multiple electro-optical converters are configurably sent to a second sensor.

3. The implantable medical device according to claim 1, wherein the at least one electrode is configured for therapeutic and/or or diagnostic purposes, wherein the electrode extends outside the hermetically sealed housing, or is situated on an exterior of the hermetically sealed housing or is part of the hermetically sealed housing.

4. The implantable medical device according to claim 3, wherein the at least one electrode is a connection to one or more of at least one sensor and at least one actuator distally situated with respect to the implantable medical device.

5. The implantable medical device according to claim 1, wherein the electro-optical converter is an optocoupler.

6. The implantable medical device according to claim 1, wherein the electro-optical converter is a sensor for electromagnetic fields which is based on optical properties of a crystal which depend on external electromagnetic fields.

7. The implantable medical device according to claim 1, wherein the electro-optical converter transfers only information concerning one or more of:
    amplitudes;
    amplitude envelopes;
    frequencies and;
    phases, in configurations having multiple electro-optical converters.

8. The implantable medical device according to claim 7, wherein the at least one detection unit for magnetic resonance tomography interference fields is configured to determine from at least one of the optical signals, a scalar value, which represents an identified field intensity, and when one or more of a presettable and a variable threshold value is exceeded or when one or more of a presettable and a variable threshold value range is reached, the at least one detection unit identifies a magnetic resonance tomography-field, wherein the scalar value is also a functional or logical linkage composed of one or more information items, such as one or more of amplitude information, frequency information, phase information, or weighted information.

9. The implantable medical device according to claim 8, wherein the information items are weighted by predetermined damping of the optical signals during transmission of the optical signals, wherein additional different dampings are utilized for different signal sources or types of information over various transmission frequencies.

10. The implantable medical device according to claim 1, further comprising multiple electrical feed lines that are connected to the electro-optical converter in series and/or in parallel.

11. The implantable medical device according to claim 1, further comprises at least one protective element wherein the electro-optical converter is connected to the at least one protective element in series and/or in parallel.

12. The implantable medical device according to claim 1, wherein the optical signals are weighted using weighting factors, and wherein the threshold for magnetic resonance tomography detection is a weighted function of a determined frequency of the induced voltages, and one or more of the threshold and weighting factors are a function of static field intensity determined via other sensors or indicators having a functional dependency that is linear or nonlinear.

13. The implantable medical device according to claim 1, wherein the magnetic resonance imaging-safe state that is switched on or initiated by the at least one detection unit is switched on for a predetermined or predeterminable time, and after the predetermined or predeterminable time elapses, said magnetic resonance imaging-safe state is deactivated, or another magnetic resonance tomography detection is performed.

14. The implantable medical device according to claim 1 further comprising any combination of one or more detection elements of
    GMR sensor,
    MagFET sensor,
    Hall sensor,
    battery voltage sensor configured to monitor voltage during capacitor charging,
    RF field detector,
    magnetic gradient field detector,
    current detector for currents induced by electromagnetic fields,
    vibration detector, for detection of vibrations induced by Lorentz forces; and,
wherein magnetic resonance tomography detection takes place only when,
    said threshold for the optical signal and/or said predetermined periodic occurrence of the optical signals is exceeded, and,
    said at least one detection unit also signals magnetic resonance tomography detection.

15. The implantable medical device according to claim 1, wherein upon magnetic resonance tomography detection or by receipt of a magnetic resonance tomography detection signal the at least one control unit is configured, to:
    change to the magnetic resonance imaging-safe state;
    remain for a prolonged period of time in the magnetic resonance imaging-safe state or a state that is insensitive to electromagnetic interference fields;
    synchronize electrical measurements through use of field intensity minimum values that occur with periodic or pulsed electromagnetic fields, or synchronize a stimulation through use of said field intensity minimum values; and,
    emit electromagnetic pulses to signal that the implantable medical device is present in an electromagnetic field, and to further signal to a magnetic resonance imaging device and transmit information regarding interference for display on a magnetic resonance imaging screen.

16. The implantable medical device according to claim 1, further comprising a position sensor, wherein said position sensor is configured for plausibility checking, such that said magnetic resonance tomography interference fields are identified only when said position sensor detects one or more of a prone posture and a presettable posture.

17. The implantable medical device according to claim 16, wherein said position sensor is self-calibrating, such that said position sensor is further configured to calibrate under presettable boundary conditions.

18. The implantable medical device according to claim 17, wherein said presettable boundary conditions comprise one or more of times of day, heart rates, respiratory rates, hemodynamic parameters and motion sensor activities.

19. The implantable device according to claim 1, wherein when the evaluation unit triggers the implantable medical device to one or more of switch to a magnetic resonance imaging-safe state, the evaluation unit is further configured to transmit a corresponding signal to the at least one control unit.

20. The implantable medical device according to claim 19, wherein said control unit is configured to change a presettable operating mode of said implantable medical device in response to said corresponding signal from said evaluation unit.

21. An implantable medical device comprising:
 a hermetically sealed housing;
 at least one control unit situated within said hermetically sealed housing;
 at least one conducting element coupled with said implantable medical device wherein said at least one conducting element comprises any combination of one or more of
  at least one electrode,
  at least one antenna,
  at least one coil;
 at least one detection unit configured to detect magnetic resonance tomography interference fields which is connected to the at least one control unit and to said at least one conducting element;
 an evaluation unit coupled with the at least one detection unit;
 wherein the at least one detection unit contains
  at least one electro-optical converter configured to convert induced voltages for said magnetic resonance tomography interference fields from said at least one conducting element to optical signals, which are optically transmitted in a potential-free manner within the detection unit to the evaluation unit;
 wherein when one or more of a threshold for the optical signals and a predetermined periodic occurrence of the optical signals is exceeded, the evaluation unit is configured to trigger the implantable medical device to one or more of switch to a magnetic resonance imaging-safe state and transmit a corresponding signal to the at least one control unit;
 wherein the optical signals are weighted using weighting factors;
 wherein the threshold for magnetic resonance tomography detection is a weighted function of a determined frequency of the induced voltages, and one or more of the threshold and weighting factors are a function of static field intensity determined via other sensors or indicators having a functional dependency that is linear or nonlinear;
 wherein the electro-optical converter transfers only information concerning one or more of:
  amplitudes;
  amplitude envelopes;
  frequencies and;
  phases, in configurations having multiple electro-optical converters;
 wherein the at least one detection unit for magnetic resonance tomography interference fields is configured to determine from at least one of the optical signals, a scalar value, which represents an identified field intensity;
  wherein the scalar value is also a functional or logical linkage composed of one or more information items, such as one or more of amplitude information, frequency information, phase information, or weighted information;
 wherein when one or more of a presettable and a variable threshold value is exceeded or when one or more of a presettable and a variable threshold value range is reached, the at least one detection unit is configured to identify a magnetic resonance tomography-field; and,
 wherein the information items are weighted by predetermined damping of the optical signals during transmission of the optical signals, wherein additional different dampings are utilized for different signal sources or types of information over various transmission frequencies.

* * * * *